(12) United States Patent
Bhargava et al.

(10) Patent No.: US 12,226,939 B2
(45) Date of Patent: Feb. 18, 2025

(54) METHOD OF PRODUCING INJECTION MOLDED ARTICLES

(71) Applicant: Alltrista Plastics, LLC, Greer, SC (US)

(72) Inventors: Saumitra Bhargava, Clarksville, MD (US); Ryan Bubb, Simpsonville, SC (US); Marty Schillinger, Simpsonville, SC (US)

(73) Assignee: ALLTRISTA PLASTICS, LLC, Greer, SC (US)

( * ) Notice: Subject to any disclaimer, the term of this patent is extended or adjusted under 35 U.S.C. 154(b) by 646 days.

(21) Appl. No.: 17/392,132

(22) Filed: Aug. 2, 2021

(65) Prior Publication Data

US 2023/0045578 A1    Feb. 9, 2023

(51) Int. Cl.
*B29C 45/13*     (2006.01)
*A61B 17/06*     (2006.01)
*B29C 45/00*     (2006.01)
*B29C 45/16*     (2006.01)
*B29C 45/18*     (2006.01)
*B29C 45/76*     (2006.01)
*B29C 45/78*     (2006.01)
(Continued)

(52) U.S. Cl.
CPC ........ *B29C 45/13* (2013.01); *A61B 17/06133* (2013.01); *B29C 45/0001* (2013.01); *B29C 45/1866* (2013.01); *B29C 45/7613* (2013.01); *B29C 45/78* (2013.01); *B29C 65/08* (2013.01); *B29C 2045/135* (2013.01); *B29C 2045/2685* (2013.01); *B29C 2945/76531* (2013.01); *B29C 2945/76558* (2013.01); *B29K 2023/065* (2013.01); *B29L 2031/712* (2013.01)

(58) Field of Classification Search
CPC ........ B29C 37/0082; B29C 2045/1659; B29C 45/164; B29C 2045/1689; B29C 2045/2685; B29C 45/13; B29C 45/1866; B29C 2045/135
See application file for complete search history.

(56) References Cited

U.S. PATENT DOCUMENTS 5,518,389 A * 5/1996 Nonomura ............... B29C 45/27
                                                            425/572
5,887,706 A * 3/1999 Pohle ................. A61B 17/06133
                                                            206/227
(Continued)

FOREIGN PATENT DOCUMENTS

CA       3025214 C  *  9/2020  ....... A61B 17/06133
EP       1048431 A1 * 11/2000  ............. B29C 45/12

OTHER PUBLICATIONS

Mechanical translation of Steinbichler EP-1048431 A1. (Year: 2000).*

*Primary Examiner* — Robert B Davis
(74) *Attorney, Agent, or Firm* — Eversheds Sutherland (US) LLP

(57) ABSTRACT

Injection molded articles and methods of making injection molded articles. The methods include the use of a first plasticizing unit and a second plasticizing unit on a common frame feeding a first mold and a second mold on the common frame. Separating the production of each part of a two-part article into separate plasticizers and molds allows for the tuning of production parameters on a per-part basis, improving part flatness and part-to-part weight variance.

19 Claims, 3 Drawing Sheets

(51) Int. Cl.
  *B29C 65/08*   (2006.01)
  *B29C 45/26*   (2006.01)
  *B29K 23/00*   (2006.01)
  *B29L 31/00*   (2006.01)

(56) References Cited

U.S. PATENT DOCUMENTS

| | | |
|---|---|---|
| 7,214,286 B2 | 5/2007 | Torris et al. |
| 7,950,127 B2 | 5/2011 | Howe et al. |
| 8,561,281 B2 | 10/2013 | Torris et al. |
| 2019/0118436 A1 | 4/2019 | Schad et al. |
| 2019/0366609 A1 | 12/2019 | Schad et al. |
| 2020/0206996 A1 | 7/2020 | Schad et al. |

* cited by examiner

METHOD OF PRODUCING INJECTION MOLDED ARTICLES

FIELD OF THE DISCLOSURE

This disclosure relates generally to injection molded articles and methods of making injection molded articles, and more particularly relates to methods of making molded articles, such as surgical suture packages, using coupled injection molding systems and methods.

BACKGROUND

Injection molding methods are typically used for the production of plastic articles in a wide range of industries. By varying the material, mold shape, including additives such as colorants, or the like, the variability of parts produced by injection molding processes is typically limited only by the cost of producing new molds.

Producing injection molded articles that involve coupling two or more separate injection molded parts presents a greater challenge. Typically, producing a two-part molded article involves two or more cavity types in a single mold, also known as "family molding." Some systems use a single plasticizer to supply two separate molds, also known as "stack molding." However, the cycle time in these processes must accommodate the larger of the two components. Thus, even if the process temperature, injection speed, mold temperature, packing pressure, and hold time is optimized for both parts, only one of the two components experiences optimum conditions due to the cycle time. As a result, part tolerances suffer, preventing the production of two-part molded articles that require high tolerances.

Separating the formation of each part of a two-part molded article into two independent molding machines has typically been avoided so as to prevent inefficiencies when a machine responsible for producing one part of a two-part molded article experiences an interruption in production. In addition, independent molding machines introduces micro variations in the machines' use and aging, which may further affect the replacement or repair schedule of the machines differently. As a result, two parts designed to be joined together experience drift in tolerances over time when they are manufactured on separate machines.

Accordingly, improved methods for producing injection molded articles are needed for overcoming one or more of the technical challenges described above.

SUMMARY

In one aspect, methods for producing injection molded articles are provided. A method includes supplying a first plasticizing unit with a first material and supplying a second plasticizing unit with a second material, wherein the first plasticizing unit and second plasticizing unit are located on a common frame. The first material is plasticized in the first plasticizing unit to produce a first molten material and the second material is plasticized in the second plasticizing unit to produce a second molten material. The first molten material is supplied to a first mold having a first plurality of cavities and the second molten material is supplied to a second mold having a second plurality of cavities, wherein the first mold and the second mold are located on the common frame. The first molten material is molded in the first plurality of cavities to produce a first plurality of injection molded parts, and the second molten material is molded in the second plurality of cavities to produce a second plurality of injection molded parts which are different from the first plurality of injection molded parts. The molded article is assembled from one part from the first plurality of injection molded parts and one part from the second plurality of injection molded parts. The molding step is conducted in a manner to produce molded parts each having a thickness with a coefficient of variance of 0.05 or less, and/or having a part-to-part weight variance of less than 1%.

In another aspect, surgical suture tray packages are provided. Surgical suture tray packages are produced by a method that includes supplying a first plasticizing unit with a first material and supplying a second plasticizing unit with a second material. The supplied material is plasticized in the first plasticizing unit to produce a first molten material and the supplied material is plasticized in the second plasticizing unit to produce a second molten material. The first molten material is supplied to a first mold having a first plurality of cavities and the second molten material is supplied to a second mold having a second plurality of cavities. The first molten material is molded in the first plurality of cavities to produce a first plurality of injection molded parts and the second molten material is molded in the second plurality of cavities to produce a second plurality of injection molded parties. A surgical suture package is assembled from a surgical suture top part and a surgical suture bottom part, the surgical suture top part selected from the first plurality of injection molded parts and the surgical suture bottom part selected from the second plurality of injection molded parts. Each part in the first plurality of injection molded parts and each part in the second plurality of injection molded parts have a thickness with a coefficient of variance of less than 0.05.

In another aspect surgical suture packages are provided. A surgical suture package includes a surgical suture top part and a surgical suture bottom part coupled using a snap-fit, wherein the surgical suture top part and the surgical suture bottom part each have a thickness with a coefficient of variance of less than 0.05, and wherein when the surgical suture top part and surgical suture bottom part are ultrasonically bonded, the force required to separate the surgical suture top part from the surgical suture bottom part is at least 15 N.

BRIEF DESCRIPTION OF THE DRAWINGS

The detailed description is set forth with reference to the accompanying drawings. The use of the same reference numerals may indicate similar to identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Injection molded articles and methods for producing injection molded articles are provided herein including coupled injection molding of articles that have improved thickness uniformity across a single part and improved article-to-article weight uniformity. In particular, it has been discovered that separating the molding of each part of a two-part article into separate plasticizer/mold assembly, and then tuning the process parameters for the specific part in that assembly, can result in thin parts having a high degree of thickness uniformity. Such uniformity substantially improves the coupling of each part in a two-part article, reducing the failure rate of the finished article. Furthermore, in a preferred embodiment, these molded articles are in the form of a surgical suture package, which is a class of molded articles that particularly benefits from improved thickness uniformity due to the higher tolerances required.

Throughout this disclosure, various aspects are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

As used herein, the term "about" with reference to dimensions refers to the dimension plus or minus 10%.

Methods of Producing Molded Articles

Figure 1:
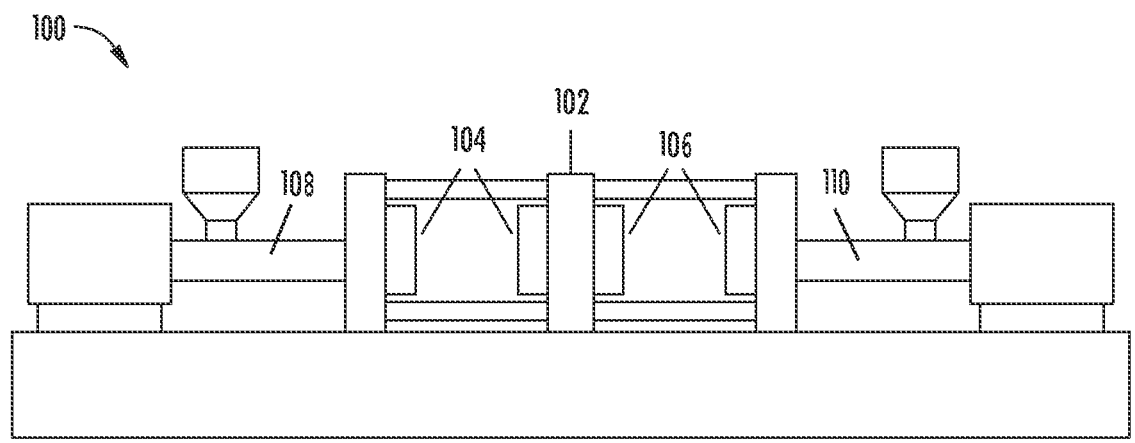
FIG. 1 is a schematic of a coupled injection molding machine in accordance with the present disclosure.

Methods of producing molded articles are disclosed herein. An example of a machine suitable for the methods described herein is shown in FIG. 1. Coupled injection molding machine 100 includes a center platen 102, first mold 104, and second mold 106. First mold 104 is supplied by a first plasticizing unit 108, and second mold 106 is supplied by a second plasticizing unit 110.

In a preferred embodiment, the method includes supplying a first plasticizing unit with a first material and supplying a second plasticizing unit with a second material. In some embodiments, the first plasticizing unit and the second plasticizing unit are located on a common frame. By utilizing both a first plasticizing unit and a second plasticizing unit that are located on a common frame, each part in a two-part article may be manufactured using individually tuned plasticizing parameters, such as a plasticizing unit melt temperature and mold fill time, without sacrificing the coupled nature characteristic of family molding and stack molding. In some embodiments, the method includes plasticizing the first material in the first plasticizing unit to produce a first molten material and plasticizing the second material in the second plasticizing unit to produce a second molten material.

As used herein, "plasticizing unit," also referred to in the industry as an "injection unit" or "extruder," refers to the component of an injection molding machine configured to accept a material, typically in the form of pellets, heat the material to create a fluid, and work the material with a screw. The result is a molten material. A plasticizing unit may be supplied by a material hopper that contains a volume of material pellets, or the plasticizing unit may be supplied by a conveyor that continuously supplied raw material. Any suitable mechanism for delivery of material the plasticizing unit may be utilized.

As used herein, "material" refers to the raw material in an injection molding process. In some embodiments, the material includes polyethylene, polypropylene, polyamide, polycarbonate, or a combination thereof. In a preferred embodiment, the material is high-density polyethylene (HDPE). The material may include additives known in the art, such as colorants, anti-oxidants, or active pharmaceutical ingredients. In some embodiments, the material is supplied to the first plasticizing unit and the second plasticizing unit in the form of pellets. In some embodiments, the first material and the second material are the same composition. In some other embodiments, the first material and the second material have different compositions from one another.

In some embodiments, the method includes supplying the first molten material to a first mold having a first plurality of cavities and supplying the second molten material to a second mold having a second plurality of cavities. In some embodiments, the first mold and the second mold are located on the common frame.

As used herein, a "cavity" in the mold corresponds to the shape of the injection molded part that is configured to be produced from the cavity. The size and number of cavities on a mold therefore depend on the size and shape of the desired injection molded part. In some embodiments, every cavity in a plurality of cavities in a single mold may correspond to the same injection molded part so that a single molding process produces a plurality of identical injection molded parts. In other embodiments, two or more different injection molded parts may be produced from a single mold.

In some embodiments, the method includes molding the first molten material in the first plurality of cavities to produce a first plurality of injection molded parts and molding the second molten material in the second plurality of cavities to produce a second plurality of injection molded parts. In some embodiments, the second plurality of injection molded parts are different from the first plurality of injection molded parts.

In some embodiments, one part from the second plurality of injection molded parts is configured to couple to one part from the first plurality of injection molded parts to form a two-part article. By utilizing both a first mold having a first plurality of cavities and a second mold having a second plurality of cavities, each part in a two-part article may be manufactured using individually tuned molding parameters, such as mold temperature, packing pressure, hold time, and cooling time, without sacrificing the coupled nature characteristic of family molding and stack molding.

In some embodiments, the method includes assembling the molded article from one part from the first plurality of injection molded parts and one part from the second plurality of injection molded parts. Assembling the molded article may include manually coupling the parts together after they have been removed from the cavities in the molds. Assembling the molded article may include the use of automation, such as through the use of robotic arms or pick-and-place robots. Any suitable means of assembling the molded article from two injection molded parts may be used.

In some embodiments, the molding step is conducted in a manner to produce molded parts each having a thickness with a coefficient of variance of 0.05 or less, having a part-to-part weight variance of less than 1%, or both.

As used herein, the "coefficient of variance" is a unitless parameter that refers to the standard deviation of a group of measurements divided by the mean of those measurements. For example, an injection molded part having an average thickness of 0.6353 mm and a thickness standard deviation of 0.0271 mm would have a coefficient of variance of 0.043. By utilizing the coefficient of variance, the uniformity of the thickness within a single part may be directly compared to other injection molded parts, regardless of the thickness of those parts. In other words, the coefficient of variance is a measure of the quality of the molding process, with a lower coefficient of variance corresponding to a high quality molding process capable of producing injection molded parts with high tolerances.

As used herein, the "part-to-part weight variance" refers to a comparison of the weight of the injection molded parts from the various "identical" cavities in a mold. For example, a hypothetical plurality of cavities that produce a plurality of injection molded parts that have the exact same weight would have 0% weight variance. However, in practice, a number of factors contribute to a part-to-part variation in weight, including small differences in the machining of the mold cavities and the distribution of molten polymer into a mold. As a result, the injection molded parts have small differences in weight, even if the cavities are designed to have identical shapes. The precise location in each individual part that is responsible for the difference in weight cannot easily be controlled or even ascertained. In other words, the reduced weight in a particular part could potentially be accounted for at a critical location within the part, such as at the location of a hinge, locking tab, or other critical feature. Depending on the intended use of the part and the assembled article, a failure in a critical feature may be costly, so parts having weights outside an acceptable range may be recycled before assembling. Therefore, reducing the weight variance of the parts produced in the various cavities of a mold will reduce the number of failed parts. In other words, the weight variance is a measure of the quality of the molding process, with a lower weight variance corresponding to a high quality molding process capable of producing injection molded parts with high consistency.

In some embodiments, the molded article produced by the method is a surgical suture package. Surgical suture packages are configured to store a suture that is wound around small stand-offs in the surgical suture package. Surgical suture packages are uniquely situated to benefit from flat injection molded parts having a consistent weight and uniform thickness. If the surgical suture package is not flat, more tension must be applied to the suture when it is wound within the suture package in order to ensure the suture stays within the package. More tension, however, will result in the suture material conforming to the stand-offs within the package and taking on a "memory" of the wound position. The suture will have bends and kinks upon removal, and will tend to curl along these bends even when installed within a patient. Flat surgical suture packages alleviate this concern by providing a path within the package for the suture to be wound without applying tension. In other words, the suture is wound around the stand-offs within the package in only two dimensions due to the flat nature of the package. Since the suture itself is 10-100 times more expensive than the package, minimizing suture failure caused by the package realizes significant cost savings.

As used herein, "flat" or "flatness" refers to uniformity in the thickness of injection molded parts. Hypothetically, an injection molded part should have 0% variation in thickness. In reality, minor variations in the machining of the mold and the distribution of molten polymer into the mold will result in small differences in the thickness of an injection molded part. As the thickness variation increases, the "flatness" of the part decreases.

In some embodiments, the first plasticizing unit and the first mold are configured using a first plurality of process parameters corresponding to the first plurality of injection molded parts. In other words, the first plasticizing unit melt temperature, fill time of the first plasticizing unit, first mold temperature, packing pressure of the first mold, hold time of the first mold, and cooling time of the first mold are selected based on the desired dimensions of the first plurality of injection molded parts. The processing parameters in injection molding applications are typically selected based the material used and the recommended parameters provided by the manufacturer. However, by separating the molding of the first plurality of injection molded parts and the second plurality of injection molded parts into separate plasticizers and separate molds, the process parameters may be separately selected based on the part. In the case of a surgical suture package, it has been unexpectedly found that the mold fill time, mold pressure, and mold temperature can be individually set for both parts of the surgical suture package and lead to substantial improvements in thickness uniformity and part-to-part weight variance.

In some embodiments, the second plasticizing unit and the second mold are configured using a second plurality of process parameters corresponding to the second plurality of injection molded parts. In other words, the second plasticizing unit melt temperature, fill time of the second plasticizing unit, second mold temperature, packing pressure of the second mold, hold time of the second mold, and cooling time of the second mold are selected based on the desired dimensions of the second plurality of injection molded parts.

In some embodiments, the fill time of the first plasticizing unit and the second plasticizing unit is 0.5 seconds or less. For example, the fill time of the first plasticizing unit may be 0.1 seconds, 0.2 seconds, 0.3 seconds, 0.4 seconds, 0.5 seconds, or any fill time in between. The fill time of the second plasticizing unit may be 0.1 seconds, 0.2 seconds, 0.3 seconds, 0.4 seconds, 0.5 seconds, or any fill time in between. The fill time of the second plasticizing unit may be the same as the fill time of the first plasticizing unit, or the fill time of the second plasticizing unit may be different from the fill time of the first plasticizing unit depending on the dimensions of the injection molded parts being produced, as described above.

In some embodiments, the hold time of the first mold and the second mold is 0.25 seconds or less. For example, the hold time of the first mold may be 0.05 seconds, 0.1 seconds, 0.15 seconds, 0.2 seconds, 0.25 seconds, or any hold time in between. The hold time of the second mold may be 0.05 seconds, 0.1 seconds, 0.15 seconds, 0.2 seconds, 0.25 seconds, or any hold time in between. The hold time of the second mold may be the same as the hold time of the first mold, or the hold time of the second mold may be different from the hold time of the first mold depending on the dimensions of the injection molded parts being produced, as described above.

In some embodiments, the first plasticizing unit melt temperature and the second plasticizing unit melt temperature are 500° F. or less. For example, the first plasticizing unit melt temperature may be 450° F., 460° F., 470° F., 480° F., 490° F., 500° F., less than 450° F., or any temperature in between. The second plasticizing unit melt temperature may be 450° F., 460° F., 470° F., 480° F., 490° F., 500° F., less than 450° F., or any temperature in between. The second plasticizing unit melt temperature may be the same as the first plasticizing unit melt temperature, or the second plasticizing unit melt temperature may be different from the first plasticizing unit melt temperature depending on the dimensions of the injection molded parts being produced, as described above.

In some embodiments, the cooling time of the first mold and the second mold is 2 seconds or less. For example, the cooling time of the first mold may be 1 second, 1.5 seconds, 2 seconds, less than 1 second, or any cooling time in between. The cooling time of the second mold may be 1 second, 1.5 seconds, 2 seconds, less than 1 second, or any cooling time in between. The cooling time of the second mold may be the same as the cooling time of the first mold, or the cooling time of the second mold may be different from the cooling time of the first mold depending on the dimensions of the injection molded parts being produced, as described above.

In some embodiments, the first mold temperature and the second mold temperature are 80° F. or less. For example, the first mold temperature may be 60° F., 70° F., 80° F., less than 60° F., or any temperature in between. The second mold temperature may be 60° F., 70° F., 80° F., less than 60° F., or any temperature in between. The second mold temperature may be the same as the first mold temperature, or the second mold temperature may be different from the first mold temperature depending on the dimensions of the injection molded parts being produced, as described above.

In some embodiments, the molded article is configured to be assembled without the need for secondary bonding. In some embodiments, the molded article is a surgical suture package and assembling the surgical suture package may be accomplished without the need for secondary bonding. Two-part molded articles typically require secondary bonding, such as ultrasonic bonding, in order to secure the two parts together. It has been unexpectedly discovered that improved flatness, thickness uniformity, and reduced part-to-part weight variance of the injection molded parts results in significant increases to part tolerances, improving the coupling of the two parts in a two-part article. As a result, secondary bonding may be eliminated entirely.

Surgical Suture Packages

Figure 2A:
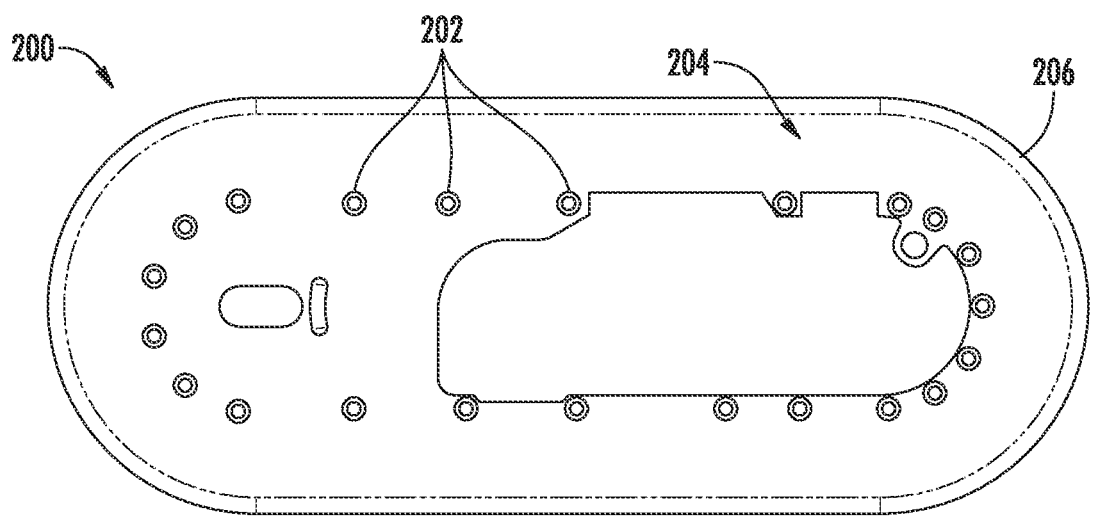
FIG. 2A is a top view of a surgical suture bottom part in accordance with the present disclosure.
Figure 2B:
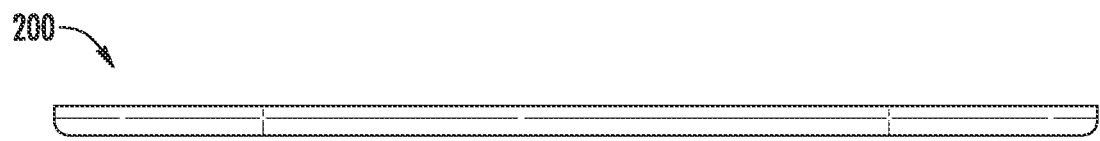
FIG. 2B is a side view of the surgical suture bottom part in FIG. 2A.
Figure 3A:
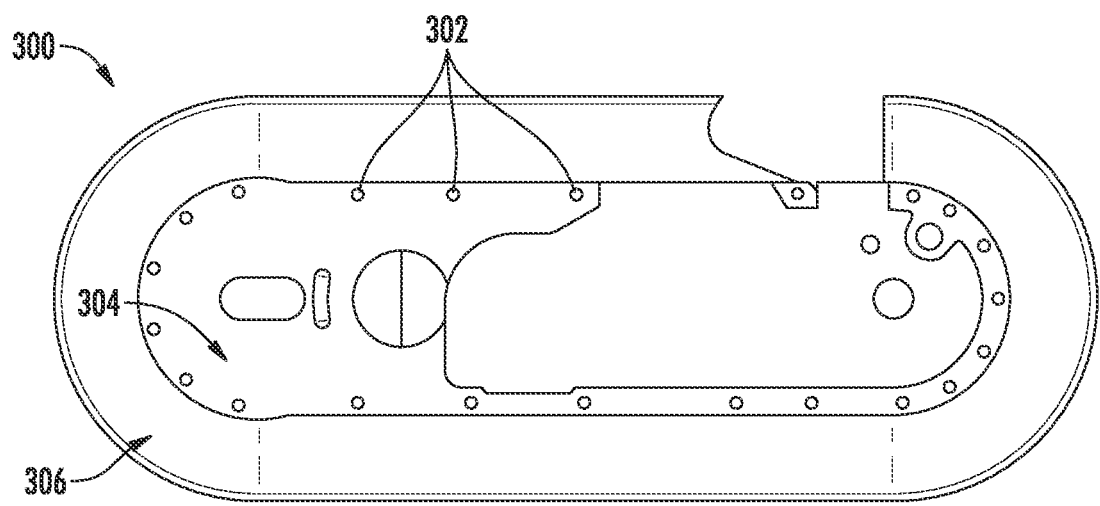
FIG. 3A is a bottom view of a surgical suture top part in accordance with the present disclosure.
Figure 3B:
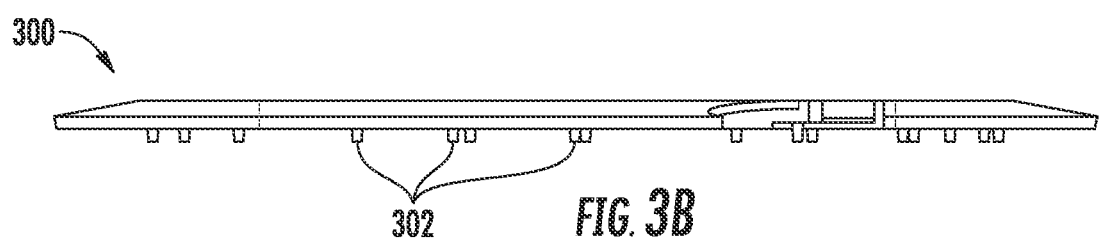
FIG. 3B is a side view of the surgical suture top part in FIG. 3A.

Surgical suture packages are also disclosed herein. An example of a surgical suture bottom part is shown in FIGS. 2A and 2B, and an example of a surgical suture top part is shown in FIGS. 3A and 3B. Both the surgical suture top part and the surgical suture bottom part generally consist of a flat body with features, such as snaps, holes, sidewalls, identifying text, and the like dispersed thereon as a result of the molding process.

In preferred embodiments, a plurality of surgical suture packages are produced by a method which includes (i) supplying a first plasticizing unit with a first material and supplying a second plasticizing unit with a second material; (ii) plasticizing the supplied material in the first plasticizing unit to produce a first molten material and plasticizing the supplied material in the second plasticizing unit to produce a second molten material; (iii) supplying the first molten material to a first mold having a first plurality of cavities and supplying the second molten material to a second mold having a second plurality of cavities; (iv) molding the first molten material in the first plurality of cavities to produce a first plurality of injection molded parts and molding the second molten material in the second plurality of cavities to produce a second plurality of injection molded parties; and (v) assembling a surgical suture package from a surgical suture top part and a surgical suture bottom part, the surgical suture top part selected from the first plurality of injection molded parts and the surgical suture bottom part selected from the second plurality of injection molded parts.

In some embodiments, each part in the first plurality of injection molded parts and each part in the second plurality of injection molded parts has a thickness with a coefficient of variance of less than 0.05. In some embodiments, the plurality of surgical suture packages have a package-to-package weight variance of less than 1%.

In some embodiments, each surgical suture package has a weight of about 3 grams. For example, the surgical suture tray may have a weight of from 1.9 grams to 7.2 grams.

In some embodiments, the surgical suture top part and the surgical suture bottom part are coupled using a snap-fit to form a surgical suture package. As used herein, a "snap-fit" refers to the interaction of a first group of features, such as a plurality of snaps, on the surgical suture top part with a second group of features, such as a plurality of holes configured to accept the plurality of snaps, on the surgical suture bottom part that results in the coupling of the two parts by "snapping" them together.

In some embodiments, each part in the first plurality of injection molded parts and each part in the second plurality of injection molded parts have an average thickness of about 0.6 mm.

In some embodiments, the plurality of surgical suture packages is formed from high-density polyethylene (HDPE).

In some embodiments, the surgical suture top part and the surgical suture bottom part are coupled without ultrasonically bonding. Two-part molded articles typically require secondary bonding, such as ultrasonic bonding, in order to secure the two parts together. It has been unexpectedly discovered that improved flatness of the surgical suture top part body and surgical suture bottom part body, thickness uniformity, and reduced part-to-part weight variance of the injection molded parts results in significant increases to part tolerances, improving the coupling of the surgical suture top part and the surgical suture bottom part in the surgical suture package. As a result, secondary bonding may be eliminated entirely.

In some embodiments, the surgical suture top part and the surgical suture bottom part are coupled with ultrasonic bonding. In some embodiments, when ultrasonic bonding is used, the force required to separate the surgical suture top part from the surgical suture bottom part is at least 15 N. Without intending to be bound by any particular theory, it is believed that the improved flatness, thickness uniformity, and part-to-part weight variance improve the tolerances of the injection molded parts. As a result, the surgical suture top part and surgical suture bottom part more readily couple together even before ultrasonic bonding, improving the quality of the ultrasonic bonding itself and improving the coupling of the parts when compared to typical manufacturing processes.

In some embodiments, each surgical suture package is characterized by a geometric stadium shape. A "geometric stadium shape" is a rectangle having a semicircle on two opposing sides. In some embodiments, the surgical suture package is suitable to wind a suture.

FIGS. 2A-2B depict an example of a surgical suture bottom part 200 and FIGS. 3A-3B depict an example of a surgical suture top part 300. Surgical suture bottom part 200 has a plurality of holes 202 configured to couple to corresponding snaps 302 in the surgical suture top part 300. Surgical suture bottom part 200 has a flat portion 204 across which the thickness of the surgical suture bottom part is measured. The flat portion 204 is surrounded by a lip 206. The thickness of the flat portion 204 of the surgical suture bottom part 200 has a coefficient of variance of 0.05 or less. Similarly, surgical suture top part 300 has a flat portion 304 across which the thickness of the surgical suture top part is measured. The thickness of the flat portion 304 of the surgical suture top part has a coefficient of variance of 0.05 or less. Surgical suture bottom part also has an angled portion 306 stretching from the flat portion 304. Angled portion 306 improves the aesthetic of the surgical suture package and serves as an indicator of the surgical suture package position when used by a user.

Figure 4:
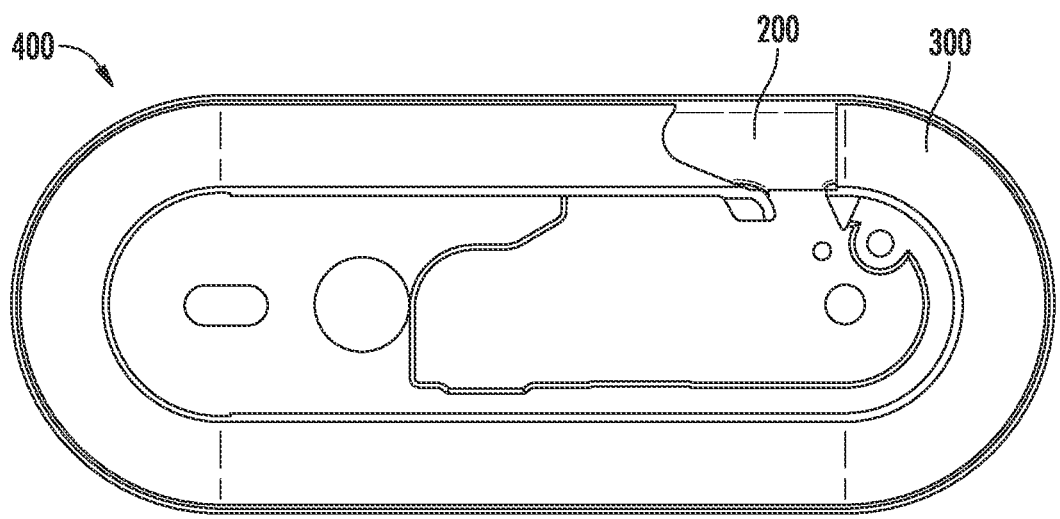
FIG. 4 is a top view of a surgical suture package in accordance with the present disclosure.

FIG. 4 depicts an example of a surgical suture package 400 formed from securing a surgical suture bottom part 200 to a surgical suture top part 300.

EXAMPLES

The invention may be further understood with reference to the following non-limiting examples.

Example 1: Comparison of Injection Molding Process with Family Molding for Surgical Suture Package Presented below in Table A are various process parameters for the method of the present disclosure and for a conventional family molding process in the production of a two-part surgical suture package. A "family molding" process is characterized by a single mold having two pluralities of cavities corresponding to two different parts. Since each part is subjected to the same process steps and parameters, the process can only be optimized (if at all) for one of the two parts, reducing the quality of at least one of the two parts. As noted previously, small differences in the machining of mold cavities can affect to part-to-part variation in weight. Although the identical mold cannot be used for both the inventive process and the family molding process, the cavities used in both processes were made by the same mold maker with identical tolerances.

TABLE A

Comparison of Process Parameters of Present Method vs. Conventional Family Molding

| | Method of the Present Disclosure 2 Separate Process Conditions | | Family Mold |
|---|---|---|---|
| | Top Part | Bottom Part | One Process |
| Plasticizer Melt Temp (° F.) | 500 | 500 | 510 |
| Mold Fill Time (Sec) | 0.49 | 0.50 | 0.65 |
| Mold Hold Time (Sec) | 0.25 | 0.25 | 0.50 |
| Mold Hold Pressure (Psi) | 14000 | 15000 | 15000 |
| Mold Temperature (° F.) | 70 | 80 | 80 |
| Cooling Time (Sec) | 1.50 | 1.50 | 2.68 |

As demonstrated in Table A, separating the molding of the surgical suture top part and the surgical suture bottom part into two separate molds allows for modification of the process parameters on a per-part basis. This results in significant time and energy savings. For example, separating the parts into their own molds allows for a reduced plasticizer melt temperature since the plurality of cavities in each mold are of a uniform size and shape. The mold fill time, hold time, and cooling times are reduced for the same reason. Furthermore, it was discovered that reducing the mold hold pressure for the surgical suture top part produced flatter parts having greater thickness uniformity. In the family mold process, these top parts would be subjected to the same pressure as the bottom part which produced less desirable results.

Example 2: Comparison of Bond Strength and Weight Variance with Family Molding

Surgical suture packages were produced as described in Example 1. The surgical suture packages were ultrasonically bonded and then pulled apart. The force required to pull the surgical suture packages apart was measured and compared to surgical suture packages produced by family molding. The results are presented in Table B.

TABLE B

Bond Strength of Surgical Suture Packages Produced by Present Method vs. Conventional Family Molding

| | Method Present Disclosure | Family Mold |
|---|---|---|
| Number of Measurements | 160 | 160 |
| Average Force Required to Separate Parts (N) | 19 | 12 |
| Standard Dev (N) | 0.84 | 1.82 |
| Q1 (N) | 18.2 | 10.9 |
| Q3 (N) | 19.6 | 13.7 |

As demonstrated in Table B, the surgical suture packages of the presently disclosed method required 58% greater force on average to separate the parts of the package than the packages produced through family molding. Furthermore, the required force was more consistent as demonstrated by the standard deviation of the force required to separate the parts, which is 54% lower than the standard deviation for the force to separate the parts of the packages produced by family molding.

Prior to testing the bond strength, the surgical suture packages of the presently disclosed method were weighed and the part-to-part variance was measured. The parts produced by the presently disclosed method had a part-to-part weight variance of 0.62%. The parts produced by family molding had a part-to-part weight variance of 1.13%.

Example 3: Comparison of Flatness Uniformity with Stack Molding

Surgical suture packages were produced as described in Example 1. The packages had a nominal weight of around 3.1 grams and dimensions of 3.73×1.50×0.11 inches. The flatness of the surgical suture bottom part were measured using a Keyence® VR5000 Precision 3D Measurement Scope using a Keyence® telecentric multi-triangulation algorithm, available commercially from Keyence Corporation, Osaka, Japan. Seven random parts from a multicavity mold were measured for each molding process. The entire surface of the part was scanned and the peaks and valleys of thickness were measured. The difference between the peaks and valleys were calculated for each cavity in the mold. The flatness uniformity was compared to surgical suture packages produced through conventional stack molding, which is a technique characterized by a two molds supplied by one plasticizer unit. The results are presented in Table C.

TABLE C

Flatness Uniformity of Surgical Suture Parts Produced by Present Method vs. Conventional Stack Mold

| | Average Deviation from nominal (mm) | Standard Deviation (mm) | Minimum (mm) in random sample | Maximum (mm) in random sample | Coefficient of Variance |
|---|---|---|---|---|---|
| Stack Mold | 1.8764 | 0.1905 | 1.648 | 2.149 | 0.10 |
| Inventive Method | 0.6353 | 0.0271 | 0.605 | 0.657 | 0.04 |

As demonstrated in Table C, the parts produced by the inventive method were 66% flatter and uniform when laying on flat surface than the parts produced by stack molding, while having a standard deviation that is 86% lower. This reduction in both the flatness and standard deviation is illustrated by the coefficient of variance, which is 60% lower for the inventive method.

Example 4: Evaluation of Temperature Effects on Weight

Since many polymers experience oxidation during processing, it is desired to minimize the processing temperature to prevent degradation of the polymer. Furthermore, some injection molded articles include an active pharmaceutical ingredient that may experience adverse effects if subjected to high temperatures. Since the processing temperature should be reduced, surgical suture packages were produced as described herein but at different plasticizer temperatures in order to evaluate the effect of plasticizer temperature on the part-to-part weight variance. The material used to form the package was high-density polyethylene. The results are presented below in Table D.

TABLE D

Comparison of Package Weight at Different Plasticizer Temperatures

| Temperature (° F.) | Average Weight (g) | Standard Deviation (g) | Minimum (g) | Q1 (g) | Q3 (g) | Maximum (g) |
|---|---|---|---|---|---|---|
| 365 | 3.2286 | 0.00559 | 3.2210 | 3.2240 | 3.2330 | 3.2390 |
| 445 | 3.1904 | 0.00831 | 3.1800 | 3.1830 | 3.1990 | 3.2020 |
| 525 | 3.1701 | 0.00840 | 3.1600 | 3.1612 | 3.1787 | 3.1790 |

As demonstrated in Table D, the temperature can be varied widely without significant negative effects on the part-to-part weight variance. It should be noted that family molding processes requires a melt temperature of between 480-540 F before the weight variance between parts grows to unacceptable levels.

While the disclosure has been described with reference to a number of embodiments, it will be understood by those skilled in the art that the disclosure is not limited to such embodiments. Rather, the disclosure can be modified to incorporate any number of variations, alterations, substitutions, or equivalent arrangements not described herein, but which are commensurate with the spirt and scope of the disclosure. Conditional language used herein, such as "can," "could," "might," or "may," unless specifically stated otherwise, or otherwise understood within the context as used, generally is intended to convey that certain embodiments include, while other embodiments do not include, certain features, elements or functional capabilities. Additionally, while various embodiments of the disclosure have been described, it is to be understood that aspects of the disclosure may include only some of the described embodiments. Accordingly, the disclosure it not to be seen as limited by the foregoing described, but is only limited by the scope of the appended claims.

That which is claimed is:

1. A method for producing a molded article, the method comprising:
supplying a first plasticizing unit with a first material and supplying a second plasticizing unit with a second material, wherein the first plasticizing unit and second plasticizing unit are located on a common frame;
plasticizing the first material in the first plasticizing unit to produce a first molten material and plasticizing the second material in the second plasticizing unit to produce a second molten material;
supplying the first molten material to a first mold having a first plurality of cavities and supplying the second molten material to a second mold having a second plurality of cavities, wherein the first mold and the second mold are located on the common frame;
molding the first molten material in the first plurality of cavities to produce a first plurality of injection molded parts, and molding the second molten material in the second plurality of cavities to produce a second plurality of injection molded parts which are different from the first plurality of injection molded parts; and
assembling the molded article from one part from the first plurality of injection molded parts and one part from the second plurality of injection molded parts,
wherein the first plasticizing unit and the first mold are configured using a first plurality of process parameters corresponding to the first plurality of injection molded parts and wherein the second plasticizing unit and the second mold are configured using a second plurality of process parameters corresponding to the second plurality of injection molded parts, such that each molded part in the first plurality of molded parts and each molded part in the second plurality of molded parts has a thickness with a coefficient of variance of 0.05 or less, and/or has a part-to-part weight variance of less than 1%.

2. The method of claim 1, wherein the molded article is a surgical suture package.

3. The method of claim 2, wherein the surgical suture package is configured to be assembled without the need for secondary bonding.

4. The method of claim 1, wherein the first material and the second material comprise polyethylene, polypropylene, polyamide, polycarbonate, or a combination thereof.

5. The method of claim 1, wherein the first material and second material have different compositions from one another.

6. The method of claim 1, wherein the first material and the second material comprise high-density polyethylene (HDPE).

7. The method of claim 1, wherein the first plurality of process parameters comprise a first plasticizing unit melt temperature, fill time of the first plasticizing unit, first mold temperature, packing pressure of the first mold, hold time of the first mold, and cooling time of the first mold.

8. The method of claim 7, wherein the fill time of the first plasticizing unit is 0.5 seconds or less.

9. The method of claim 7, wherein the hold time of the first mold is 0.25 seconds or less.

10. The method of claim 7, wherein the first plasticizing unit melt temperature is 500° F. or less.

11. The method of claim 7, wherein the cooling time of the first mold is 2 seconds or less.

12. The method of claim 7, wherein the first mold temperature is 80° F. or less.

13. The method of claim 1, wherein the second plurality of process parameters comprise a second plasticizing unit melt temperature, fill time of the second plasticizing unit, second mold temperature, packing pressure of the second mold, hold time of the second mold, and cooling time of the second mold.

14. The method of claim 13, wherein the fill time of the second plasticizing unit is 0.5 seconds or less.

15. The method of claim 13, wherein the hold time of the second mold is 0.25 seconds or less.

16. The method of claim 13, wherein the second plasticizing unit melt temperature is 500° F. or less.

17. The method of claim 13, wherein the cooling time of the second mold is 2 seconds or less.

18. The method of claim 13, wherein the second mold temperature is 80° F. or less.

19. The method of claim 1, wherein the molding step is conducted in a manner to produce molded parts each having a thickness with a coefficient of variance that is at least 50% lower than a coefficient of variance of thickness for parts produced by stack molding.

* * * * *